United States Patent
Bender, II et al.

(10) Patent No.: US 11,197,973 B2
(45) Date of Patent: Dec. 14, 2021

(54) SYSTEM AND METHOD FOR MONITORING FILLING STATUS OF A VAPORIZER RESERVOIR IN AN ANESTHETIC VAPORIZER SYSTEM

(71) Applicant: GE Precision Healthcare LLC, Wauwatosa, WI (US)

(72) Inventors: Thomas Lane Bender, II, Madison, WI (US); Brady Weigel, Madison, WI (US)

(73) Assignee: GE Precision Healthcare LLC, Wauwatosa, WI (US)

(*) Notice: Subject to any disclaimer, the term of this patent is extended or adjusted under 35 U.S.C. 154(b) by 368 days.

(21) Appl. No.: 16/273,624

(22) Filed: Feb. 12, 2019

(65) Prior Publication Data

US 2020/0254210 A1 Aug. 13, 2020

(51) Int. Cl.
| | |
|---|---|
| *A61M 16/18* | (2006.01) |
| *A61M 16/20* | (2006.01) |
| *A61M 16/08* | (2006.01) |
| *A61M 39/26* | (2006.01) |
| *B65D 47/24* | (2006.01) |

(52) U.S. Cl.
CPC .......... *A61M 16/183* (2013.01); *A61M 16/20* (2013.01); *A61M 16/0816* (2013.01); *A61M 39/26* (2013.01); *A61M 2205/6045* (2013.01); *B65D 47/24* (2013.01)

(58) Field of Classification Search
CPC .. A61M 16/00; A61M 16/0051; A61M 16/01; A61M 16/024; A61M 16/104; A61M 16/162; A61M 16/164; A61M 16/18; A61M 16/183; A61M 16/186; A61M 16/20; A61M 2205/18; A61M 2205/3396; A61M 2209/045
See application file for complete search history.

(56) References Cited

U.S. PATENT DOCUMENTS

| | | |
|---|---|---|
| 8,522,839 B2 | 9/2013 | Freed et al. |
| 8,528,550 B2 | 9/2013 | Cuzyldo et al. |

(Continued)

FOREIGN PATENT DOCUMENTS

| | | |
|---|---|---|
| EP | 2645070 A2 | 10/2013 |
| WO | 2007103658 | 9/2007 |

(Continued)

OTHER PUBLICATIONS

PCT application PCT/US2020/017626 filed Feb. 11, 2020—International Search Report/Written Opinion dated Jun. 4, 2020, 11 pages.

*Primary Examiner* — Joseph D. Boecker
(74) *Attorney, Agent, or Firm* — Andrus Intellectual Property Law, LLP

(57) ABSTRACT

An anesthetic vaporizer system includes a reservoir containing anesthetic agent, an agent level sensor measuring an agent level of the anesthetic agent in the reservoir, a display, and a controller. The controller is configured to receive agent level measurements from the agent level sensor over a time period, and determine the anesthetic agent is being added to the reservoir from an agent source based on the agent level measurements over the time period. A filling status is determined based on the agent level measurements and a filling status indicator is displayed based on the determined filling status.

18 Claims, 6 Drawing Sheets

(56) References Cited

U.S. PATENT DOCUMENTS

| | | |
|---|---|---|
| 8,783,248 B2 | 7/2014 | Heinonen et al. |
| D741,879 S | 10/2015 | Chapman et al. |
| 9,186,478 B2 | 11/2015 | Schnaars et al. |
| 2010/0000958 A1 | 1/2010 | Mitchell et al. |
| 2010/0269820 A1* | 10/2010 | Danielsen ............. A61M 16/18 128/202.22 |
| 2011/0031313 A1* | 2/2011 | Faber ................... A61M 16/186 235/462.01 |
| 2011/0056490 A1* | 3/2011 | Kullik ................... A61M 16/18 128/203.12 |
| 2011/0102796 A1* | 5/2011 | Shang .................. A61M 16/183 356/436 |
| 2011/0186046 A1* | 8/2011 | Rindy .................. A61M 16/183 128/203.14 |
| 2013/0255676 A1* | 10/2013 | Kuehl ..................... G01F 23/02 128/203.12 |
| 2015/0250961 A1* | 9/2015 | Whitman .......... A61M 16/0051 600/411 |
| 2015/0320116 A1 | 11/2015 | Bleloch et al. |
| 2016/0361514 A1 | 12/2016 | Warby |
| 2017/0182281 A1 | 6/2017 | Kersey et al. |
| 2017/0259026 A1 | 9/2017 | Mair et al. |

FOREIGN PATENT DOCUMENTS

| | | |
|---|---|---|
| WO | 2008151667 | 12/2008 |
| WO | 2010147843 | 12/2010 |
| WO | 2016059038 | 4/2016 |

* cited by examiner

SYSTEM AND METHOD FOR MONITORING FILLING STATUS OF A VAPORIZER RESERVOIR IN AN ANESTHETIC VAPORIZER SYSTEM

BACKGROUND

The present disclosure generally relates to systems and methods of monitoring the amount of anesthetic agent in a vaporizer reservoir, and more specifically, to methods and systems of monitoring and reporting filling status of a vaporizer reservoir when anesthetic agent is added to the reservoir from an agent source.

An anesthesia system may be implemented to deliver a predetermined dosage of anesthetic agent to a patient. The anesthesia system may be pneumatically connected to a vaporizer. Conventional vaporizers comprise a reservoir, sometimes called a "sump", adapted to retain a liquid anesthetic agent and a vaporization chamber that converts the liquid anesthetic agent into a gas. The gaseous anesthetic agent is inhaled into the patient's lungs to produce an effect, such as pain management, unconsciousness, preventing memory formation, and/or paralysis.

An anesthesiologist or other user monitors the level of anesthetic agent in the vaporizer to ensure sufficient anesthetic agent is available for treatment of a patient. As the anesthetic agent is vaporized, the liquid level of the anesthetic goes down. Some means is provided for a visual approximation of the level of anesthetic agent remaining in the vaporizer, such as a sight glass or a digital level indicator. When the anesthetic agent becomes low, the user will add more anesthetic agent to the reservoir from an agent source, which is typically a bottle of anesthetic agent. The reservoir has a fill port, and the bottle or other agent source is connected to the fill port in order to pour anesthetic agent into the reservoir.

SUMMARY

This Summary is provided to introduce a selection of concepts that are further described below in the Detailed Description. This Summary is not intended to identify key or essential features of the claimed subject matter, nor is it intended to be used as an aid in limiting the scope of the claimed subject matter.

In one embodiment, an anesthetic vaporizer system includes a reservoir containing anesthetic agent, an agent level sensor measuring an agent level of the anesthetic agent in the reservoir, a display, and a controller. The controller is configured to receive agent level measurements from the agent level sensor over a time period, and determine the anesthetic agent is being added to the reservoir from an agent source based on the agent level measurements over the time period. A filling status is determined based on the agent level measurements and a filling status indicator is displayed based on the determined filling status.

One embodiment of a method for monitoring filling status of a vaporizer reservoir in an anesthetic vaporizer system includes providing a reservoir configured to contain anesthetic agent to be dispensed by an anesthetic vaporizer system and an agent level sensor measuring an agent level of the anesthetic agent in the reservoir. Agent level measurements are received over a time period from the agent level sensor at a controller. Steps executed by the controller include determining that anesthetic agent is being added to the reservoir from an agent source based on the agent level measurements over the time period, determining a filling status based on the agent level measurements, and then controlling a display to display a filling status indicator accordingly.

Various other features, objects, and advantages of the invention will be made apparent from the following description taken together with the drawings.

BRIEF DESCRIPTION OF THE DRAWINGS

The present disclosure is described with reference to the following Figures.

DETAILED DESCRIPTION

The inventors have recognized a problem relating to certain anesthetic agent sources, or anesthetic agent bottles, and particularly with agent sources that have a non-transparent casing where it is difficult to see the agent through the casing. Where agent sources are not transparent, it can be difficult to know how much agent is left in the source, such as the bottle, when the source is attached to the reservoir during the refill process. For example, it is difficult for a user to know when a bottle has been completely emptied and can be removed from the vaporizer. To provide one example, Baxter has introduced a new Desflurane bottle that is aluminum and thus is not transparent. Accordingly, the inventors developed a system and method whereby the filling process of the vaporizer reservoir is monitored using one or more sensors and logic to determine and notify a user of the filling status. For example, the system may be configured to determine and notify a user that agent is currently being inserted into the reservoir—a currently filling status. Likewise, the system may be configured to determine and indicate that the fill process has been completed and that the reservoir is sufficiently full—a reservoir full status. Similarly, the system may be configured to determine that an agent source is attached to the fill port but that no agent is being added to the reservoir—an empty bottle status. Other exemplary filling statuses may also be determined and indicated, such as determining and indicating that a bottle has been attached to the vaporizer, or determining and indicating that a bottle containing anesthetic agent remains attached to the vaporizer while the vaporizer is in use. In the latter instance, which is not an intended use for the vaporizer, the system may generate an alert to prompt a user to remove the bottle from the fill port.

The inventors have also recognized that the filling status information can be stored, aggregated, and collected to measure certain usage and performance indicators. For example, the filling status information may be aggregated and stored in a log, a filling status log, which may be stored locally on an anesthesia system or in a vaporizer system, or may be stored on a hospital network. Such information may used to determine usage and performance indicators, such as a number of fills during a life of a vaporizer system. Additionally, fill pattern information may be identified based on the aggregated filling status information, such as how often a reservoir was filled, how much agent was added on average during a fill session, what the agent level in the reservoir was prior to filling, or the like. Similarly, the aggregated information can be utilized to identify common misuse scenarios, such as where an anesthetic source containing agent is left attached to the fill port while the vaporizer is in use.

Figure 1:
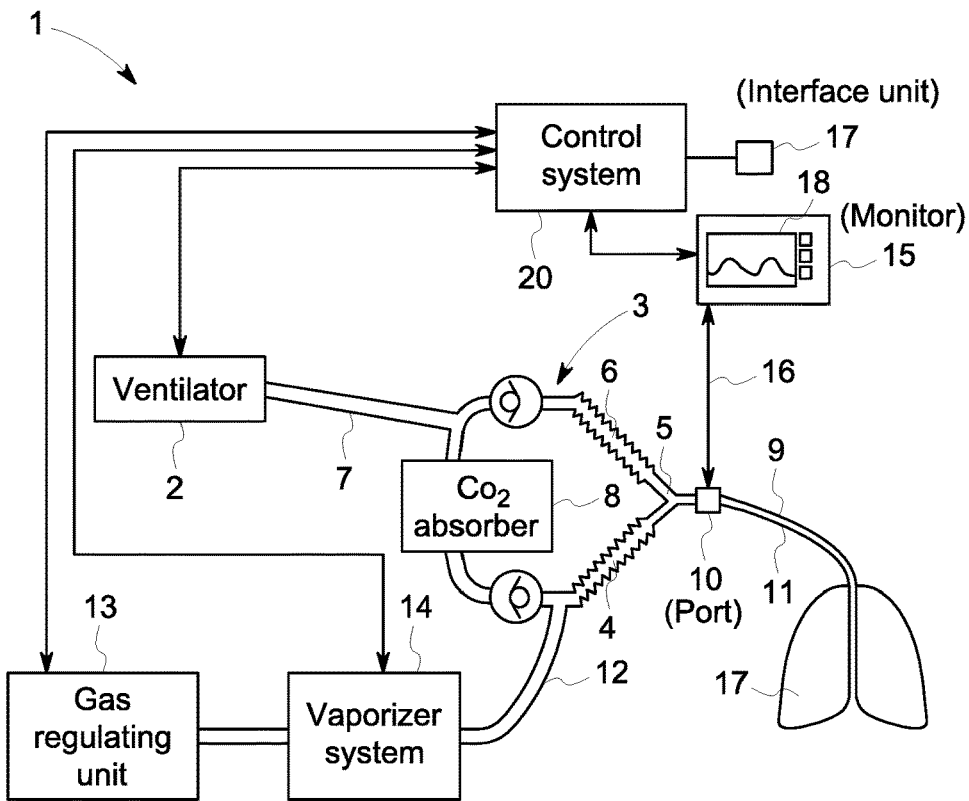
FIG. 1 schematically depicts an exemplary anesthesia system that includes an anesthetic vaporizer system according to one embodiment of the present disclosure.

FIG. 1 exemplifies the disclosed system and method for determining fill status of a vaporizer reservoir, which is utilized within an anesthesia environment and in connection with a vaporizer system. The ventilator 2 fills patient lungs during inspiration by pressurizing the breathing circuit 3. The breathing circuit includes inspiration limb 4, Y-piece 5, expiration limb 6, ventilator limb 7, $CO_2$ absorber 8, and patient limb 9. Inspiration and expiration limbs 4, 6 each include a unidirectional valve to direct the inspiration and expiration gas flow to respective limbs. Patient limb 9 includes gas monitor sampling port 10 and intubation tube 11 connecting the patient with the breathing circuit. In operation, ventilator receives the expired gas from the patient during expiration and stores the gas for the next inspiration. At inspiration the gas is guided through $CO_2$ absorber, where the $CO_2$ is removed, to inspiration limb and further to patient lungs. Breathing gas is brought into the breathing circuit from fresh gas line 12. The breathing gas is a mixture of $O_2$, $N_2O$ or $N_2$ (air) from gas regulating unit 13, and volatile agents vaporized into this gas stream in the vaporizer 14. Alternatively patient may be breathing spontaneously. In spontaneous breathing, the ventilator comprises a reservoir collecting the exhalation gas and the patient breathing action receives inspiration gas therefrom.

Figure 2:
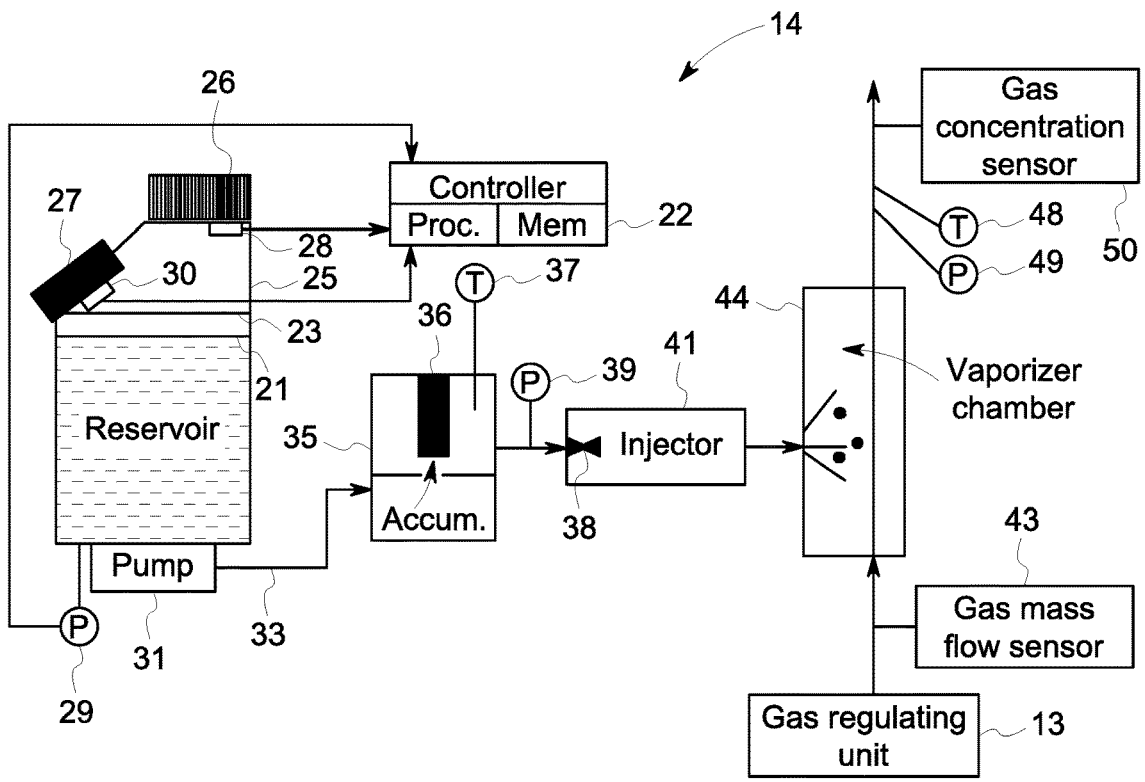
FIG. 2 depicts an exemplary vaporizer system configured to monitor filling status according to one embodiment of the present disclosure.

Monitor device 15, i.e. gas monitor, may be of a sidestream type drawing a sample gas stream from the sampling port 10 through sampling line 16 for analysis with the sensors within the monitor. Alternatively the monitor device 15 may be of mainstream type where the gas analysis sensors are located directly at the patient limb instead of the sampling port. Monitor device 15 is further electrically connected to control system 20, which is further connected to the actuators (gas regulating unit 13, and/or vaporizer 14) closing the control loop. This control system 20 compares the measured values with the set target, which may be user-set targets or software-controlled targets, and tunes the actuators to match the measured values with the setting. For example, the user can set and/or adjust the target by using an interface unit 17. In certain embodiments, the concentration setting 56 may be controlled by a setting of the dial 26, such as provided at the top of the vaporizer reservoir 25 (FIG. 2). In other embodiments, the concentration setting 56 may be inputted by a clinician, such as via an interface unit 17 for the anesthesia system 1 or directly for the vaporizer system 14.

FIG. 2 depicts one embodiment of a vaporizer system 14 of the anesthesia system 1. The vaporizer system 14 includes a vaporizer reservoir 25 that houses liquid anesthetic agent to be dispensed for inhalation by the patient, such as into the breathing circuit 3 for the patient. The vaporizer reservoir 25 is filled by inserting additional anesthetic agent through the fill port 27 from an agent source, such as by pouring anesthetic agent from a refill bottle into the vaporizer reservoir 25. The reservoir 25 includes one or more agent level sensors 28, 29 for measuring an amount of anesthetic agent, or agent level 21, in the reservoir 25.

The agent level sensors 28, 29 may be any of various types of sensors capable of determining the level of liquid anesthetic agent in the vaporizer reservoir 25. For example, the agent level sensor 28 may be a time-of-flight infrared or ambient light sensor. To provide just one example, the agent level sensor 28 may be a proximity and ambient light sensing module, such as the VL 6180 X sensor by STMicroelectronics N. V. As an alternative example, the agent level sensor 28 may be an ultrasonic sensor, such as positioned on a top side of the interior of the vaporizer reservoir 25.

In the depicted example, a pressure sensor 29 senses a pressure exerted by the anesthetic agent at the bottom of the vaporizer reservoir 25, which can be used as an agent level sensor as well. Based on the known properties of the liquid anesthetic agent, the agent level 21 can be determined based on the pressure measured by the pressure sensor 29. The pressure sensor 29 may be, for example, a differential pressure transducer (DP) measuring a high pressure at the bottom of the vaporizer reservoir 25 and a low pressure at a top of the vaporizer reservoir 25. Thereby, the pressure sensor 29 can measure a difference between the gas pressure at the top of the vaporizer reservoir 25 and the combined gas and liquid level pressure at the bottom of the vaporizer reservoir 25. Thereby, the liquid pressure can be isolated, which can provide a liquid level measurement. When determining the liquid level based on the liquid pressure measurement, specific gravity is preferably taken into account. The agent level 21 may be provided by the following equation, where pressure is the hydrostatic head pressure measured at the bottom of the vaporizer reservoir 25 (cm water column, psi, bar, etc.) and the specific gravity is the specific gravity of the specific liquid anesthetic agent contained in the vaporizer reservoir 25:

$$\text{Agent Level} = \frac{\text{Pressure}}{\text{Specific Gravity}}$$

$$\text{Specific Gravity} = \frac{\text{Density of Agent}}{\text{Density of Water}}$$

The resulting agent level 21 is then provided as a height of the liquid being measured, such as in centimeters or millimeters.

The one or more pressure sensors 29 may also be utilized to determine when an agent source is connected to the reservoir 25. Namely, when an agent source, such as a refill bottle, is connected, the pressure sensor 29 will sense a change in pressure. Depending on the temperature inside the reservoir and the temperature inside the anesthetic agent bottle, the pressure inside both chambers will vary, but the pressures in the reservoir and the agent bottle are unlikely to be equal prior to connecting the two together. Thus, when an agent source is connected to the fill port 27, the pressure inside the vaporizer reservoir will change depending on the relative pressure inside the agent source. Such a pressure change can be used to identify connection of an agent source.

Figure 3:
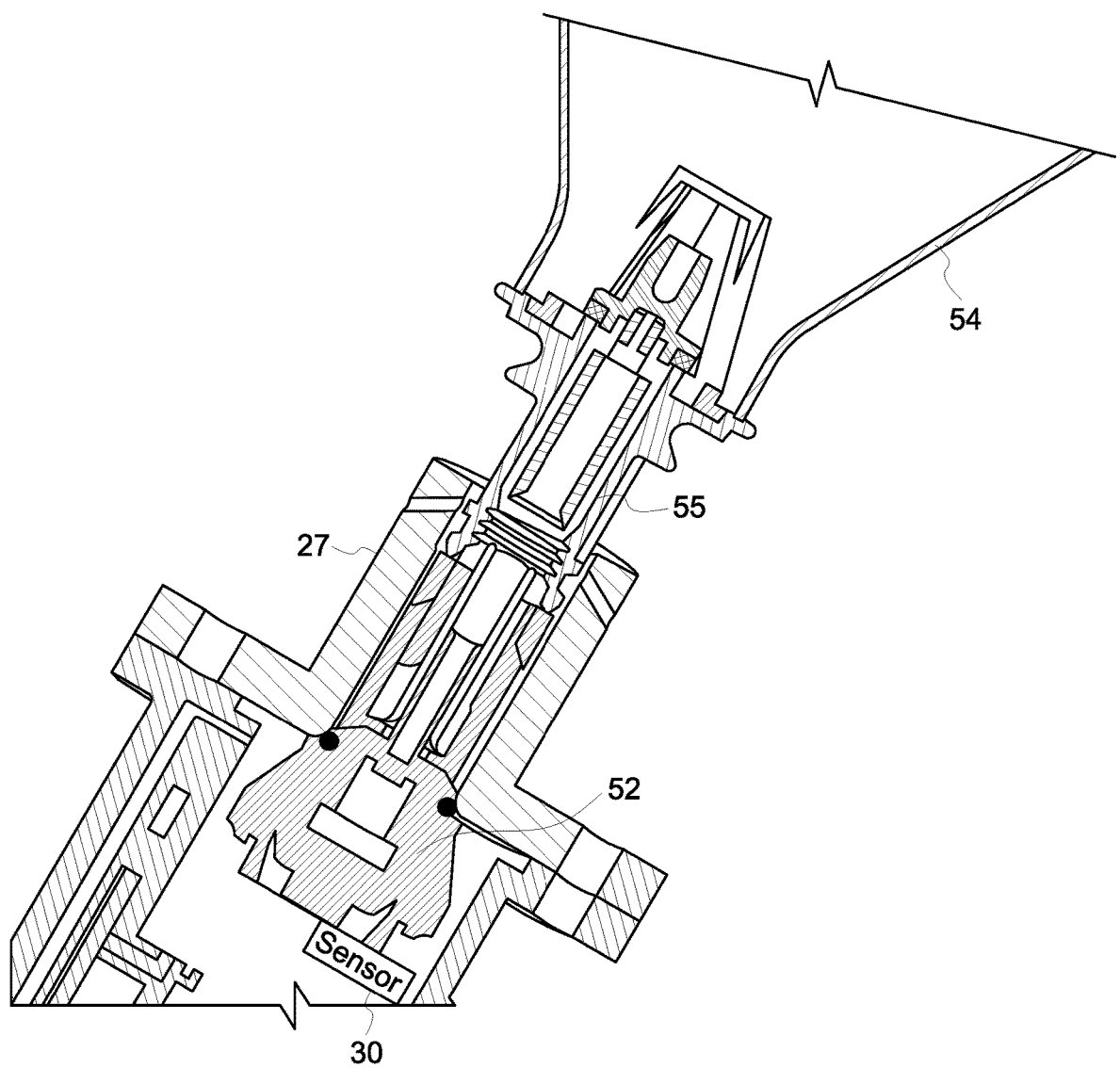
FIG. 3 depicts a fill port of a vaporizer reservoir according to one embodiment of the present disclosure.

Alternatively or additionally, a valve position sensor 30 may be positioned on a valve at the fill port 27. As shown in FIG. 3, the fill port 27 has a valve 52 that opens upon connection of an anesthetic source 54, which in the depicted embodiment is an anesthetic bottle. The anesthetic bottle 54 has a nozzle 55 that, when placed into the fill port 27 depresses the fill valve 52 into an open position. Anesthetic agent can then be evacuated from the agent source 54 into the vaporizer reservoir 25 in order to refill the reservoir 25. A valve position sensor 30 may be positioned on or adjacent to the fill valve 52 in order to measure the valve position—i.e. whether the fill valve 52 is open or closed. The valve position sensor may be any sensor configured to differentiate between the open and closed valve position of the fill valve 52. In one embodiment, the valve position sensor 30 may be a capacitive sensor. In other embodiments, the valve position sensor 30 may be an inductive or magnetic sensor or other type of sensor for sensing valve position, such as an infrared or ultrasonic sensor configured to sense position of the fill valve 52. The valve position sensor 30 may be configured to distinguish whether the fill vale 52 is open or closed, or may be configured to track the valve position over a range of positions from fully open to fully closed. Such information may be utilized by the controller 22 to assist in determining filling status.

Output of the valve position sensor 30, agent level sensor 28, and pressure sensor 29 are provided to the controller 22. Referring again to FIG. 2, the controller 22 is configured to use the information measured by the sensors in order to determine when anesthetic agent is being added to the reservoir and to determine a filling status based on those measurements. The controller 22 is configured to determine and advise a user of the filling status, such as to identify a current filling status, a reservoir full status, an empty bottle status, and/or an improper use status, such as where an agent source containing an aesthetic agent remains attached to the fill port 27 while the vaporizer system 14 is in use to dispense agent to the patient.

The controller may be a stand-alone control device associated with the reservoir 25 of the vaporizer system 14, or may be integrated into and comprise part of the control system 20 for the anesthesia system 1 or other system that incorporates the vaporizer system 14. The controller 22 comprises a processor and memory for storing computer executable instructions, or software, and other data. For example, a filling status log may be stored in memory of the controller 22, or some other storage device associated with the controller 22, that stores the sensor information and/or the filling status information identified based on the sensor measurements. In certain embodiments, service technicians may obtain the service log information from the memory associated with the controller 22, such as via a USB connection or a Bluetooth® connection to the controller 22 and/or the control system 20. In other embodiments, the controller 22 and/or control system 20 may be connected by wired or wireless means to a hospital network and may communicate the service log information thereto such that the service log information may be stored on the hospital network.

A pump 31 is connected to the vaporizer reservoir 25 to pump liquid through the supply line 33 to the accumulator 35. Liquid anesthetic agent is accumulated at the accumulator to a particular pressure. The liquid anesthetic agent in the accumulator 35 is heated by heater 36 to a set temperature. The heated and pressurized liquid anesthetic agent is then injected into a gas flow in the vaporizer chamber 44. Specifically, the liquid anesthetic agent is provided through an injector 41 into the vaporizer chamber 44, where it becomes anesthetic vapor and mixes with the fresh gas supplied to the vaporizer chamber 44 from the gas regulating unit 13. Dispensing of the anesthetic agent through the injector 41 is controlled by opening and closing of the valve 38 to provide a specified amount of anesthetic agent in order to meet a concentration setting 56. Namely, depending on the amount of fresh gas being supplied by the gas regulating unit 13, the valve 38 is controlled to dispense a specified amount of anesthetic agent into the fresh gas stream in order to reach a concentration setting 56, such as an anesthesia concentration setting set by a clinician. As will be understood by a person having ordinary skill in the art in light of the present disclosure, the period and frequency of the valve 38 opening can be controlled, in consideration of the pressure and temperature of the anesthetic agent, in order to deliver a precise amount of anesthetic agent into the gas stream in the vaporizer chamber 44. As will also be understood by a person having ordinary skill in the art in light of the present disclosure, certain embodiments may employ other dispensing means for dispensing the anesthetic agent into the gas stream for delivery to the patient. Several such dispensing means are known in the art, such as an accumulator/dispenser comprising a diaphragm separating a liquid anesthetic volume from a gas volume.

The vaporizer system 14 includes various sensors configured to assist in determining a dispense rate of anesthetic agent. The sensors provide information to a controller 22 configured to determine and track filling status of the reservoir. In various embodiments, the controller 22 may be a separate control device housed locally in the vaporizer system 14, or the controller 22 may be incorporated in the control system 20 for the anesthesia system 1. In still other embodiments, the vaporizer system 14 may be incorporated within other patient care systems or devices, such as a critical care ventilator or a bypass machine. In such embodiments, the controller 22 may be housed locally within the vaporizer system 14, or may be provided within the control system of a relevant host device.

In the example of FIG. 2, sensors are provided to measure information regarding or relating to the amount of anesthesia that is being dispensed to the patient, such as to determine a dispense rate and/or a dispensed agent amount. A gas temperature sensor 48 is configured to measure a temperature 59 of the mixed gas provided from the vaporizer chamber 44. A gas pressure sensor 49 is configured to measure pressure 60 of the mixed gas provided from the vaporizer chamber 44. A gas concentration sensor 50 is configured to measure the anesthetic concentration in the mixed gas provided from the vaporizer chamber 44, which is the anesthetic concentration of the gas outputted from the vaporizer system 14, such as through the gas line 12 (FIG. 1). In other embodiments, the gas concentration sensor 50 may be eliminated, and the dispense rate and/or dispensed agent amount may instead be calculated based on a concentration setting 56 for controlling delivery of anesthetic agent in the mixed gas provided from the vaporizer chamber 44. A gas mass flow sensor 43 is also provided, and configured to measure a gas flow rate 58 entering or exiting the vaporizer chamber 44. In the depicted embodiment, the gas mass flow sensor 43 is provided between the gas regulating unit 13 and the vaporizer chamber 44, and thus is configured to measure the gas flow rate 58 of the fresh gas entering the vaporizer chamber 44. In other embodiments, the gas mass flow sensor 43 may be provided to measure the gas flow rate 58 of gas that has exited the vaporizer chamber 44, such as providing the gas mass flow sensor 43 at or near the gas concentration sensor 50. Accordingly, the dispense rate and/or dispensed agent amount is calculated based on the gas flow rate 58, the mixed gas pressure 60, the mixed gas temperature 59, and the anesthetic concentration (which may be the anesthetic agent concentration measured by the gas concentration sensor 50, or may be a concentration setting 56, or liquid agent mass flow measurement between the accumulator and the injector 41). In one embodiment, a sensor pack may be provided at the output of the vaporizer chamber 44, such as along the gas line 12 between the vaporizer system 14 and the breathing circuit 3, providing the gas temperature sensor 48, the gas pressure sensor 49, the gas concentration sensor 50, and the gas mass flow sensor 43.

In still further embodiments, dispense rate and/or dispensed agent amount may be based on other values, such as information measured at the injector 41 and/or the accumulator 45. A temperature sensor 37 may be provided at the accumulator 35 (or alternatively at any location providing a sufficiently accurate measurement of temperature of the liquid anesthetic agent provided to the injector 41), which provides an injector temperature 64 measurement of the temperature of liquid anesthetic agent provided to the injector 41. A pressure sensor 39 is configured to measure the pressure of anesthetic agent provided to the injector 41 through the valve 38. An injection frequency 66 is also provided, which is the rate and duration that the valve 38 is open to dispense anesthetic agent into the vaporizer chamber 44 from the injector 41. Alternatively or additionally, the dispense rate can be determined based on information measured at the vaporizer reservoir 25. For example, the dispense rate may be calculated as a trend determination based on agent level measurements 68 by one or more agent level sensors 28, 29.

The controller determines filling status and other filling information based on the measured sensor values, and may also make determinations based on the dispense rate or an operation state of the anesthetic vaporizer system—e.g. whether it is currently operating to vaporize and dispense anesthetic agent from the reservoir 25 to the patient or is not currently operating to dispense anesthetic agent.

Figure 4:
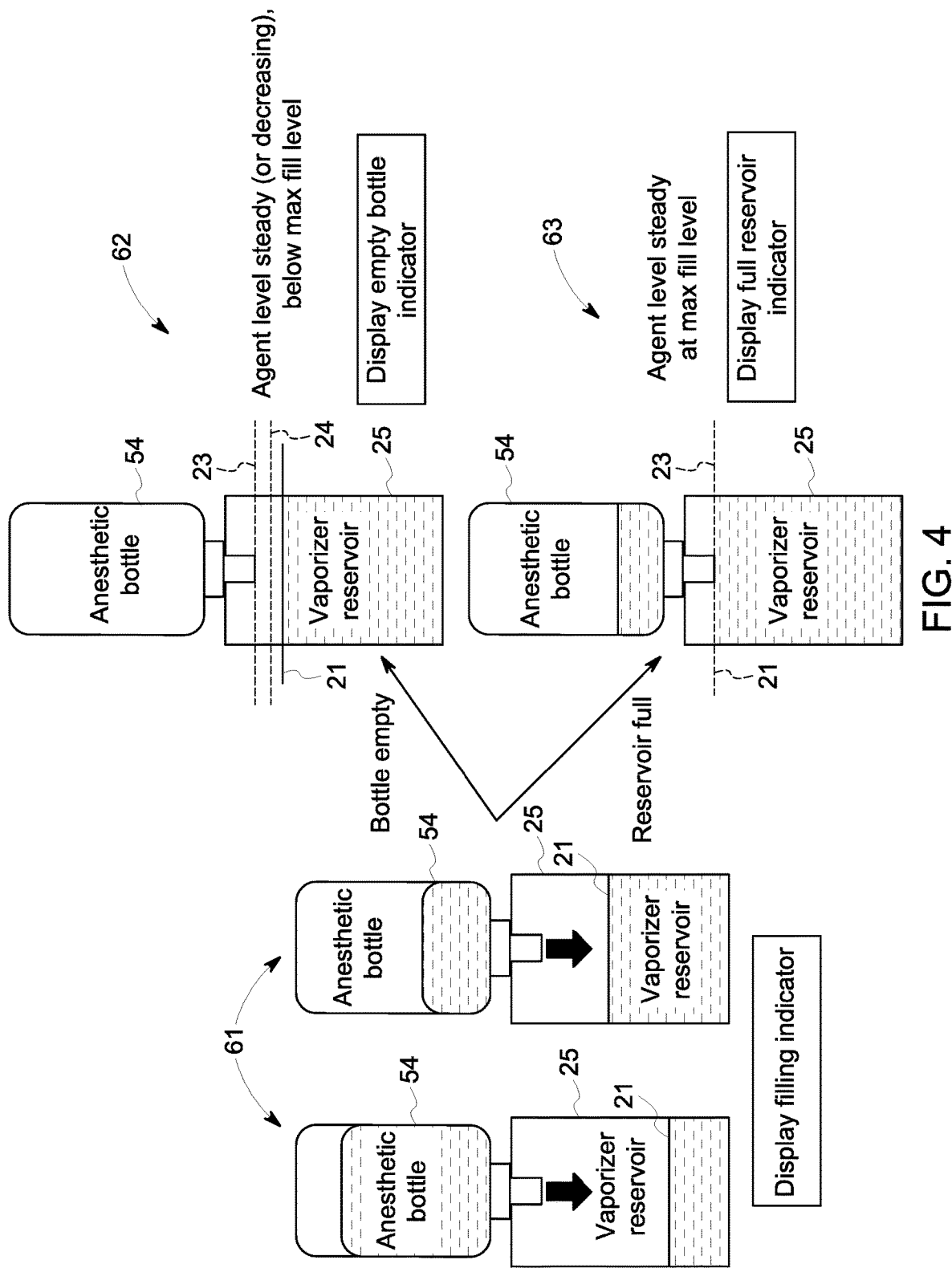
FIG. 4 is a schematic diagram depicting various filling conditions and corresponding filling statuses according to one example of the present disclosure.

FIG. 4 exemplifies three filling statuses, including a currently filling status 61, a full reservoir status 63, and an empty bottle status 63. When the controller 22 determines, based on a detection of rising agent level measurements over a time period, that anesthetic agent is being added to the reservoir 25 from an agent source 54. The controller 22 is further configured to, upon detection of a rising agent level 21 in the reservoir 25, determine a filling status. When the agent level 21 measurements by the agent level sensor 28, 29 rise, meaning that agent is being inserted into the reservoir 25, the controller 22 determines a currently filling status 61. For example, the controller 22 may be configured to detect an increase in agent level 21 over a predetermined number of measurement intervals by the agent level sensor 28, 29. If the agent level 21 stops rising, becoming stationary or decreasing, and the agent level 21 is less than a maximum fill level 23, then the controller may assign an empty bottle status 62. In certain embodiments, if the agent level 21 is less than a threshold fill level 24, then the controller may further determine that additional anesthetic agent should be added to the reservoir 25 and may prompt the user accordingly. In one embodiment, the threshold fill level 24 is a predetermined amount less than the maximum fill level. For instance, the threshold fill level may be 5 milliliters less than the maximum fill level. In other embodiments, the difference between the threshold fill level 24 and the maximum fill level 23 may be greater or less than 5 milliliters.

If the controller senses that the agent level 21 equals the maximum fill level 23, then the controller may assign a full reservoir status 63. In certain embodiments, if the agent level 21 is equal to the maximum fill level 23, the controller 22 may be configured to conduct further analysis to determine whether an impermissible or unintended use is occurring where the agent source 54 remains attached to the vaporizer reservoir 25 during operation and continues to fill the reservoir 25 as agent is removed from the reservoir 25 via the vaporization process. In such an embodiment, an alert may be generated to advise the user to remove the anesthetic source 54 from the fill port 27. For example, such an alert may be generated via the display 18 on the monitor 15 for the anesthesia system 1. Alternatively or additionally, an auditory alert may be generated, which may be generated from the speaker associated with the monitor 15 or interface unit 17 for the anesthesia system 1, or may be a speaker associated with the vaporizer system 14 in particular.

The controller 22 may be configured to display a filling status indicator that corresponds with the determined filling status, various examples of which are described herein. In one example, a filling indicator may be displayed during periods where the currently filling status 61 is identified. Similarly, an empty bottle indicator may be displayed when the empty bottle status 62 is identified, and a full reservoir indicator may be displayed when the full reservoir status 63 is identified. Each indicator may be, for example, a dialogue displayed on the digital display 18, such as a status box stating "filling", "empty bottle", or "full reservoir." Alternatively or additionally, during the currently filling status 61, the filling indicator may be or include a countdown displayed indicating the amount of time until the reservoir is full.

Figure 5:
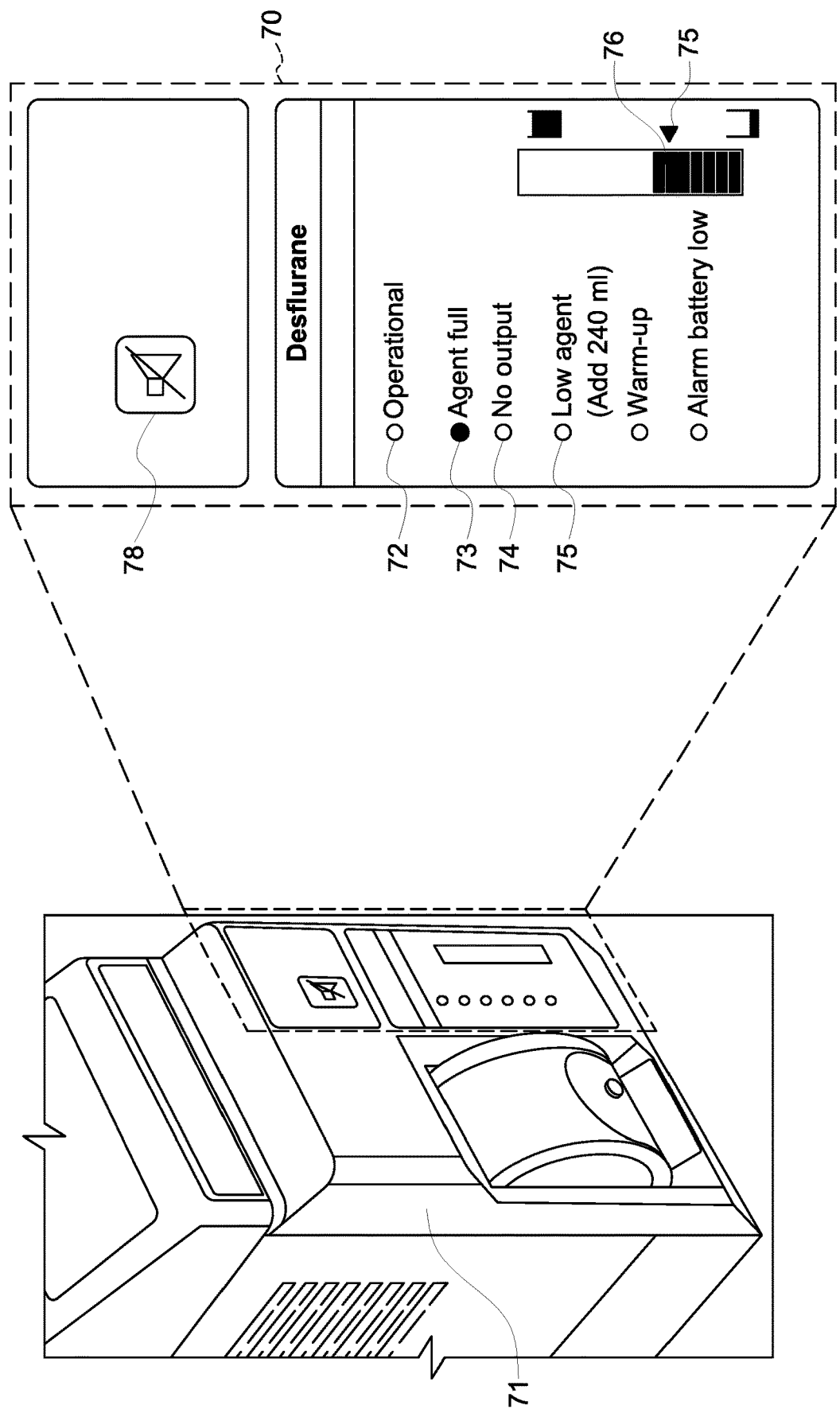
FIG. 5 provides one example of a display on a reservoir housing according to one embodiment of the present disclosure.

FIG. 5 depicts another exemplary embodiment of a display, which may be an alternative to or in addition to use of the digital display 18. The display 70 is on the housing 71 surrounding the vaporizer reservoir 25. The user interface display 70 includes multiple LED's, each LED illuminable to indicate system information, including filling status information. In the depicted example, an operation state LED 72 is illuminable to indicate that the vaporizer system 14 is operating to dispense an aesthetic agent. A full reservoir status indicator 73 is an LED illuminable to indicate when the agent level 21 in the reservoir is at the maximum fill level 23. In certain embodiments, the full reservoir status indicator 73 may remain illuminated while the agent level 21 is within a predetermined distance of the maximum fill level 23, such as plus or minus 1 milliliter.

LED 74 is another operation state indicator, which is illuminable to indicate when the vaporizer system 14 is not providing any agent output. A low agent indicator 75 is an LED illuminable to indicate that agent should be added to the reservoir 25. In certain embodiments, the low agent indicator 75 may be configured to illuminate the LED when there's room for a full bottle of agent in the reservoir 25. A normal volume for a bottle of anesthetic agent ranges from 100 milliliters (ml) to 250 ml. Vaporizer reservoirs come in various sizes but are typically between 100 ml and 415 ml. Thus, where the low agent indicator 75 is configured to turn on when a full bottle can be added to the reservoir 25, the low agent indicator 75 will illuminate well before the agent level 21 in the reservoir 25 becomes critically low. A second low agent indicator 75' is also provided in the example at FIG. 5, where an arrow or mark is provided next to the LED agent level display 76 to demarcate where the full bottle refill level is. In other embodiments, the level display may instead be a sight glass rather than an LED display. Finally, the user interface display 70 on the housing 71 further includes an auditory alarm mute button 78, such as to silent alarms generated to indicate misuse cases, error states, etc.

Figure 6:
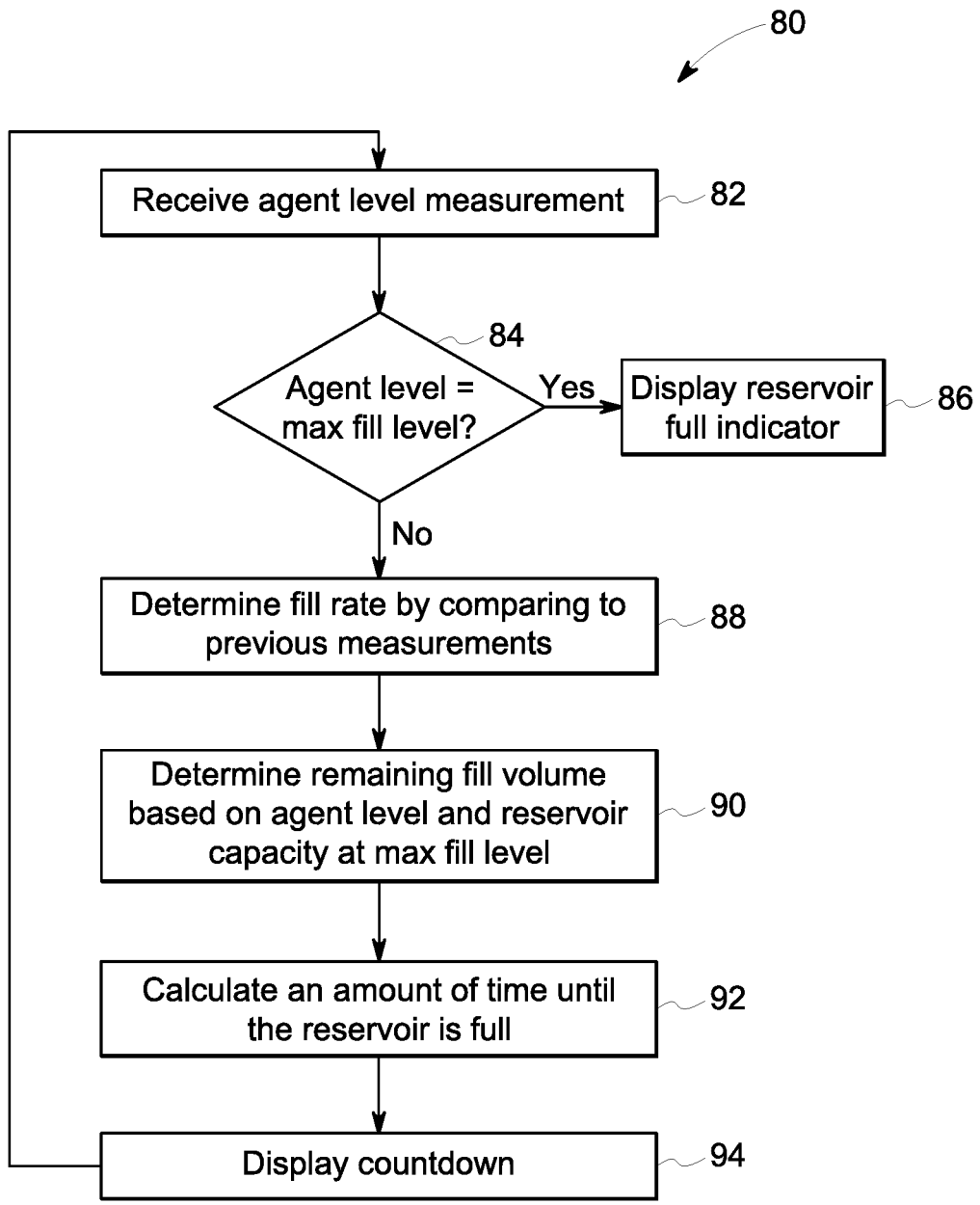
FIG. 6 is a method flow chart depicting one embodiment of a method of monitoring filling status of a vaporizer reservoir.

FIG. 6 depicts one embodiment of a method 80 of monitoring filling status of a vaporizer reservoir 25 where a fill countdown is determined and displayed. A new agent level measurement is received at step 82. Instructions are executed at step 84 to determine whether the agent level has reached the maximum fill level. If so, then a reservoir full status indicator is displayed at step 86, such as by illuminating the agent full LED indicator 73. If the agent level has not reached the maximum fill level at step 84, then a fill rate is determined at step 88 by comparing the new agent level measurement to previous agent level measurements such that a change in agent level over time is determined. A remaining fill volume is determined at step 90 based on the most recent agent level measurement and a reservoir capacity at maximum fill level. An amount of time until the reservoir is full can then be calculated at step 92 based on the fill rate and the remaining fill volume. A countdown of the remaining time is then displayed at step 94. The controller continues to measure fill level and calculate the remaining amount of time until the reservoir is full, and updating the countdown accordingly until the agent level reaches the full indicator. Alternatively, the controller may detect that the agent level is stable or decreasing, at which point the empty bottle indicator would be displayed.

Figure 7:
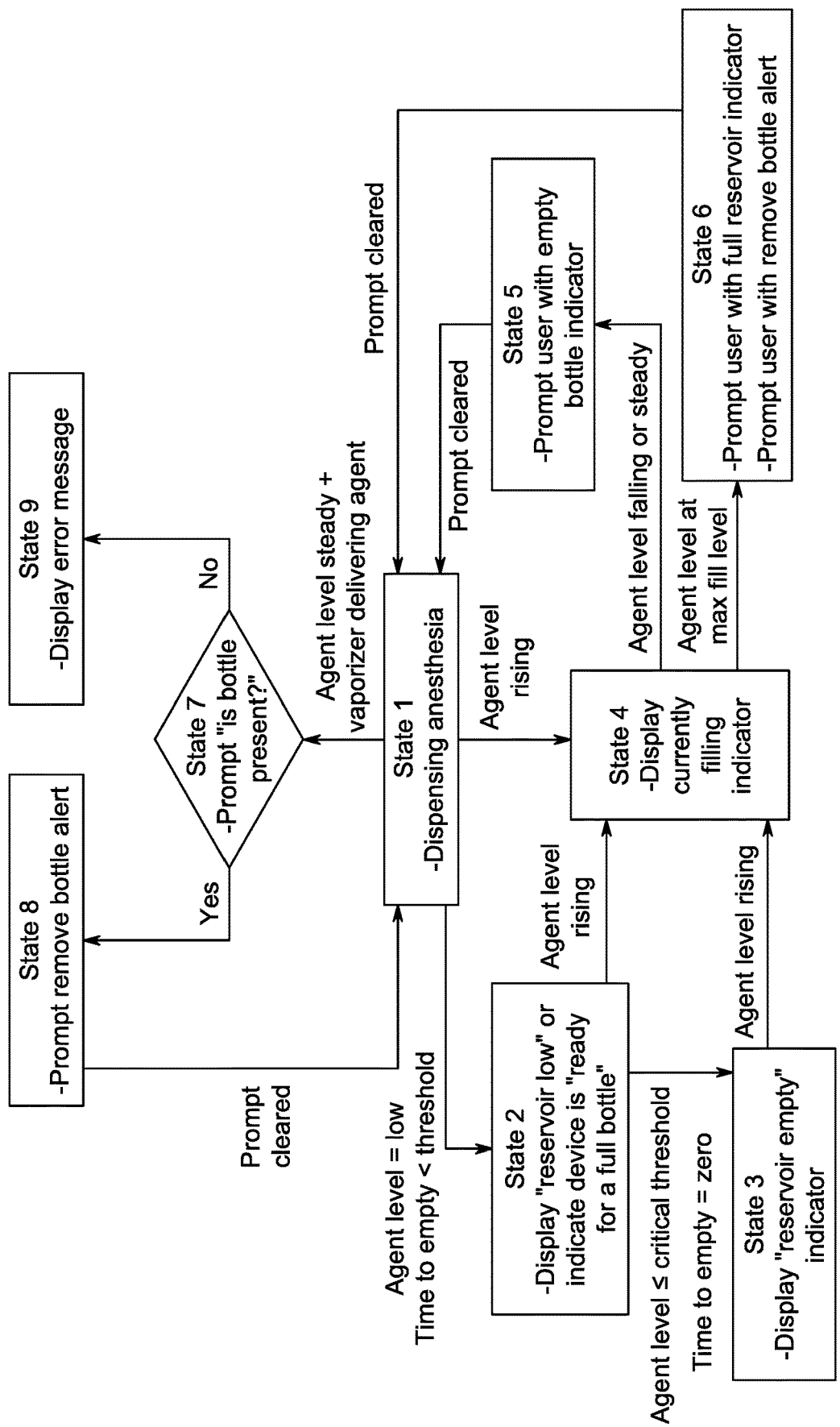
FIG. 7 is a state diagram exemplifying one embodiment of a method of monitoring filling status of a vaporizer reservoir.

FIG. 7 is a state diagram depicting another embodiment of a method for monitoring fill status of a vaporizer reservoir. At State 1, the vaporizer system 14 is operating to dispense anesthesia to a patient. Thus, the agent level 21 will generally be decreasing as the agent is pumped from the reservoir 25 to the vaporizer chamber 44. The controller 22 continues to receive agent level 21 measurements from the one or more agent level sensors 28, 29. Eventually the agent level may become low, such as reaching the low agent level where a full bottle of agent can be added to the reservoir 25. Alternatively, the low agent level may be determined based on a calculated time to empty, such as exemplified in FIG. 6. For example, if the time to empty reaches a threshold level, the controller 22 may determine that the agent is low. Once the low agent status is detected, the controller proceeds to State 2 and displays the reservoir low indictor, such as displaying a dialogue box stating "ready for a full bottle" and/or illuminating the low agent LED indicator 75. If no agent is added, then the agent level 21 will become even lower, eventually reaching a critically low threshold. At such an agent level, the time to empty may be 0, or a very low number, such as a few minutes or even one minute. At that point, the controller 22 proceeds to State 3, and displays a reservoir empty indicator. As described above, the various indicators may be provided by the digital display 18 on the monitor 15, by a digital display associated with the vaporizer system 14 in particular, and/or by the LEDs on the user interface display 70 on the housing 71 for the reservoir 25.

If the controller senses, such as based on agent level measurements by the agent level sensor 28, that the agent level is increasing, then the controller determines that an anesthetic agent is being added to the reservoir 25 from an agent source 54 and proceeds to State 4. The currently filling indicator is then displayed. In certain embodiments, the currently filling indicator may be a countdown of the amount of time until the reservoir is full. In the currently filling status 61, State 4, the agent level 21 will be rising. If the agent level is no longer rising, and becomes steady or begins to decrease, then the controller 22 proceeds to State 5 which is the empty bottle status 62. An empty bottle indicator may be displayed, which may include a visual or auditory prompt instructing the user to remove the empty bottle from the reservoir. The controller may also determine based on the agent level 21 whether additional agent is needed, such as based on whether the agent level 21 is less than the threshold fill level 24. If the prompt is cleared then the controller returns to State 1 and continues dispensing anesthesia.

If the controller 22 is at State 4 and the agent level 21 reaches a maximum fill level 23, then the full reservoir status 63 is reached, represented at State 6. The full reservoir indicator is then displayed, which may be accompanied by a prompt to bring the user's attention to the fact that the reservoir is full and that the agent source 54, which still contains agent, needs to be removed. Once the prompt is cleared, the controller returns to State 1 and continues dispensing anesthesia according to normal operating functionality.

As described above, it is not intended or approved for a vaporizer system 14 to be continually operated with an agent bottle or agent source attached. Thus, if the prompt is cleared after State 6 but the anesthesia source 54 is not removed from the fill port 27, then the agent source 54 will continually fill the reservoir 25 to a maximum fill level as agent is pumped from the reservoir 25 and vaporized. The controller 22 may be configured to detect such a condition. In embodiments having a valve position sensor 30 on the fill valve 52, detection of the continued presence of the agent source 54 may be determined based on the valve position. For example, the controller 22 may be configured to provide a predetermined amount of time after the prompt is cleared before regenerating the remove bottle alert. Alternatively, the presence of the agent source 54 can be detected in embodiments with no valve position sensor 30 based on the agent level and the operation state of the vaporizer system 14. Namely, if the vaporizer 14 is operating to dispense agent, but the agent level is not decreasing, then the controller may determine that agent continues to be added to the reservoir 25 and thus the agent source 54 remains attached. In certain embodiments, the controller 22 may compare the agent level to a dispensed amount, calculated as described above, to determine whether the agent level is decreasing by an expected amount according to how much agent is being dispensed.

If the agent level is not decreasing as expected, then the controller 22 may proceed to State 7 which prompts the user to indicate whether a bottle is present. For example, the prompt may be generated via a digital display 18 associated with the anesthesia delivery system 1. In another embodiment, the prompt may be via a user interface associated with the vaporizer system, such as an auditory alert via a speaker associated with the vaporizer system 14 in conjunction with a visual indicator prompting a user to provide input to indicate whether a bottle is present. If the input indicates that a bottle is present, then the controller proceeds to State 8, which is associated with the misuse scenario where an agent source 54 remains attached to the fill port 27 while the vaporizer system 14 is in use. The remove bottle alert will be regenerated. The controller returns to State 1 once the remove bottle alert is cleared. To provide one example, an alert may be cleared via the user interface display 70 on the housing 71 via the alarm mute button 78. Alternatively or additionally, the systems 1, 14 may be configured to receive other user inputs to clear the alert, such as via the interface unit 17 or the monitor 15. If, at State 7, the user indicates that a bottle is not present, then the controller 22 detects that an error has occurred and proceeds to State 9. An error message is displayed, which may be via the user interface 70 on the housing 71 and/or via the digital display 18 on the monitor 15. Such an error may be caused, for example, by a faulty agent level sensor 28, 29 not currently measuring the agent level 21.

At each state, the status may be stored in a filling status log, such as in memory of the controller 22. The status may be stored in conjunction with a time stamp of such status determination, and may also be stored in conjunction with certain measurement data upon which the status was determined. In certain embodiments, the status log may then be utilized to generate a filling trend based on the fillings status values stored therein. For example, the filling trend may indicate a progression of filling times and/or filling amounts over a certain time period or over the life of the vaporizer system 14. Such information may be useful to identify problems related to vaporizer filling, such as relating to problems with the fill valve 52. For example, increased fill times and/or decreased fill rates may be associated with degradation of the fill valve 52, such as a faulty seal, or may indicate that debris is stuck in the fill valve. In either case, such information will be useful for servicing the vaporizer system 14. Additionally, the fill status log and filling trend may provide information regarding fill patterns for the vaporizer system 14, such as a number of fills per time period, how much agent is added to the reservoir 25 on average, how low the agent level 21 is when the reservoir 25 gets filled, or the like. Such information may be useful for identifying areas where clinicians and/or technicians should be trained to better operate the vaporizer system 14, and may also identify common misuse scenarios so that intervention or design changes may be made accordingly.

This written description uses examples to disclose the invention, including the best mode, and also to enable any person skilled in the art to make and use the invention. Certain terms have been used for brevity, clarity and understanding. No unnecessary limitations are to be inferred therefrom beyond the requirement of the prior art because such terms are used for descriptive purposes only and are intended to be broadly construed. The patentable scope of the invention is defined by the claims, and may include other examples that occur to those skilled in the art. Such other examples are intended to be within the scope of the claims if they have features or structural elements that do not differ from the literal language of the claims, or if they include equivalent features or structural elements with insubstantial differences from the literal languages of the claims.

We claim:

1. An anesthetic vaporizer system comprising:
    a reservoir containing anesthetic agent;
    an agent level sensor measuring an agent level of the anesthetic agent in the reservoir;
    a display;
    a controller configured to:
        receive agent level measurements from the agent level sensor over a time period;
        determine that anesthetic agent is being added to the reservoir from an agent source based on the agent level measurements over the time period;
        determine a fill rate based on the agent level measurements over the time period;
        determine a filling status based on the agent level measurements, including calculate an amount of time until the reservoir is full based on the fill rate and the agent level; and
        display a filling status indicator on the display based on the determined filling status, including display a countdown of the amount of time until the reservoir is full.

2. The anesthetic vaporizer system of claim 1, wherein the filling status is one of a currently filling status, a full reservoir status, and an empty bottle status.

3. The anesthetic vaporizer system of claim 1, wherein the controller is further configured to:
    detect that the agent level is no longer increasing;
    determine that the agent source is empty; and
    display an empty bottle status indicator.

4. The anesthetic vaporizer system of claim 1, wherein the controller is further configured to detect that the agent level has reached a maximum fill level and then display a full reservoir status indicator.

5. The anesthetic vaporizer system of claim 4, wherein the full reservoir status indicator includes an LED indicator configured to illuminate when the agent level reaches the maximum fill level, and/or wherein the display is a digital display controllable to indicate any one of a currently filling status indicator, the full status indicator, and an empty bottle status indicator.

6. The anesthetic vaporizer system of claim 4, wherein the controller is further configured to:
    determine that the agent source is not empty based on the fill level and an operation state of the anesthetic vaporizer system;
    generate a remove bottle alert to alert a user to remove the agent source from the reservoir.

7. The anesthetic vaporizer system of claim 1, wherein the controller is further configured to:
    store the filling status to generate a filling status log; and
    determine a filling trend based on the filling status values in the filling status log.

8. The anesthetic vaporizer system of claim 1, wherein the controller is further configured to:
    detect that the agent level is stable or decreasing;
    determine that the agent level is less than a threshold fill level; and
    display an empty bottle indicator.

9. The anesthetic vaporizer system of claim 1, further comprising at least one of a valve position sensor configured to sense a position of a fill valve of the reservoir and a pressure sensor configured to sense a pressure change in the reservoir;
    wherein the controller is further configured to determine the filling status based further on the position of the fill valve or the pressure change in the reservoir.

10. The anesthetic vaporizer system of claim 9, wherein the controller is further configured to:
    detect that the agent level has reached a threshold fill level;
    detect, based on the position of the fill valve measured by the valve position sensor, that the agent source remains connected to the reservoir;
    determine that the agent source is not empty based on the fill level and an operation state of the anesthetic vaporizer system; and
    generate a remove bottle alert instructing a user to remove the agent source from the reservoir.

11. A method for monitoring filling status of a reservoir in an anesthetic vaporizer system, the method comprising:
    providing the reservoir configured to contain anesthetic agent and an agent level sensor measuring an agent level of the anesthetic agent in the reservoir;

receiving, at a controller, agent level measurements over a time period from the agent level sensor;

determining, with the controller, that anesthetic agent is being added to the reservoir from an agent source based on the agent level measurements over the time period;

determining, with the controller, a fill rate based on the change in the agent level over the time period;

determining, with the controller, a filling status based on the agent level measurements wherein determining the filling status includes calculating an amount of time until the reservoir is full based on the fill rate and the agent level; and controlling a display to display a filling status indicator based on the filling status wherein displaying the filling status indicator includes displaying a countdown of the amount of time until the reservoir is full.

12. The method of claim 11, wherein the filling status is one of a currently filling status, a full status, and an empty bottle status.

13. The method of claim 11, further comprising:
detecting that the agent level is no longer increasing;
determining that the agent source is empty; and
displaying an empty bottle status indicator.

14. The method of claim 11, further comprising detecting that the agent level has reached a threshold fill level and then displaying a full reservoir indicator.

15. The method of claim 14, further comprising:
determining that the agent source is not empty based on the fill level and an operation state of the anesthetic vaporizer system; and
generating a remove bottle alert instructing a user to remove the agent source from the reservoir.

16. The method of claim 11, further comprising:
detecting that the agent level is stable or decreasing;
determining that the agent level is less than a fill threshold; and
displaying an empty bottle indicator.

17. The method of claim 11, further comprising:
receiving a valve position of a fill valve of the reservoir from a valve position sensor; and
determining the filling status based further on the position of the fill valve.

18. The method of claim 17, further comprising:
detecting that the agent level has reached a threshold fill level;
detecting, based on the position of the fill valve, that the agent source remains connected to the reservoir;
determining that the agent source is not empty based on the fill level and an operation state of the anesthetic vaporizer system; and
generating a remove bottle alert instructing a user to remove the agent source from the reservoir.

* * * * *